United States Patent
Fayyaz et al.

(10) Patent No.: US 8,403,883 B2
(45) Date of Patent: Mar. 26, 2013

(54) MEDICAL INJECTOR WITH DOSE KNOB ACTIVATION FOR AUTOMATED RECONSTITUTION

(75) Inventors: Asif Fayyaz, Paramus, NJ (US); Richard A. Cronenberg, Mahwah, NJ (US); Lionel Vedrine, Palo Alto, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/119,014

(22) PCT Filed: Sep. 18, 2009

(86) PCT No.: PCT/US2009/057439
§ 371 (c)(1),
(2), (4) Date: Nov. 1, 2011

(87) PCT Pub. No.: WO2010/033778
PCT Pub. Date: Mar. 25, 2010

(65) Prior Publication Data
US 2012/0041366 A1   Feb. 16, 2012

Related U.S. Application Data

(60) Provisional application No. 61/192,466, filed on Sep. 18, 2008.

(51) Int. Cl.
*A61M 37/00* (2006.01)
*A61M 5/20* (2006.01)
(52) U.S. Cl. .......................... 604/90; 604/135
(58) Field of Classification Search ............... 604/82–92, 604/131, 134–137
See application file for complete search history.

(56) References Cited

U.S. PATENT DOCUMENTS

| | | | |
|---|---|---|---|
| 4,689,042 A * | 8/1987 | Sarnoff et al. | 604/89 |
| 6,270,479 B1 | 8/2001 | Bergens et al. | |
| 6,793,646 B1 * | 9/2004 | Giambattista et al. | 604/90 |
| 7,407,494 B2 * | 8/2008 | Bostrom et al. | 604/207 |
| 8,092,420 B2 * | 1/2012 | Bendek et al. | 604/89 |
| 2005/0277885 A1 | 12/2005 | Scherer | |
| 2006/0184117 A1 | 8/2006 | Knight et al. | |
| 2006/0270985 A1 | 11/2006 | Hommann et al. | |

* cited by examiner

*Primary Examiner* — Nicholas Lucchesi
*Assistant Examiner* — Nathan R Price
(74) *Attorney, Agent, or Firm* — Hoffmann & Baron, LLP

(57) ABSTRACT

A medical injector is provided herein having a body and a reservoir disposed in the body, the reservoir including at least first and second mixable components. At least one stopper is associated with the reservoir where distal advancement of the stopper over a predetermined distance causes mixing of the mixable components. A plunger is disposed in the body, along with a knob stem and a knob fixed to the knob stem so as to be rotatable therewith. A sleeve is telescopingly disposed over the knob stem, wherein the knob stem and the sleeve have cooperating elements formed thereon which selectively permit rotation of the knob stem to be transmitted to the sleeve so that the knob stem and the sleeve may rotate together. A spring is also provided for urging the sleeve distally. A releasable retainer releasably retains the sleeve against force of the spring. Rotation of the knob releases the sleeve and allows the spring to displace the sleeve distally. Distal movement of the sleeve causes distal movement of the plunger which causes distal movement of the stopper thus causing mixing of the mixable components. Advantageously, with the subject invention, a medical injector may be provided where autoreconstitution can be achieved by the turning of a knob.

4 Claims, 3 Drawing Sheets

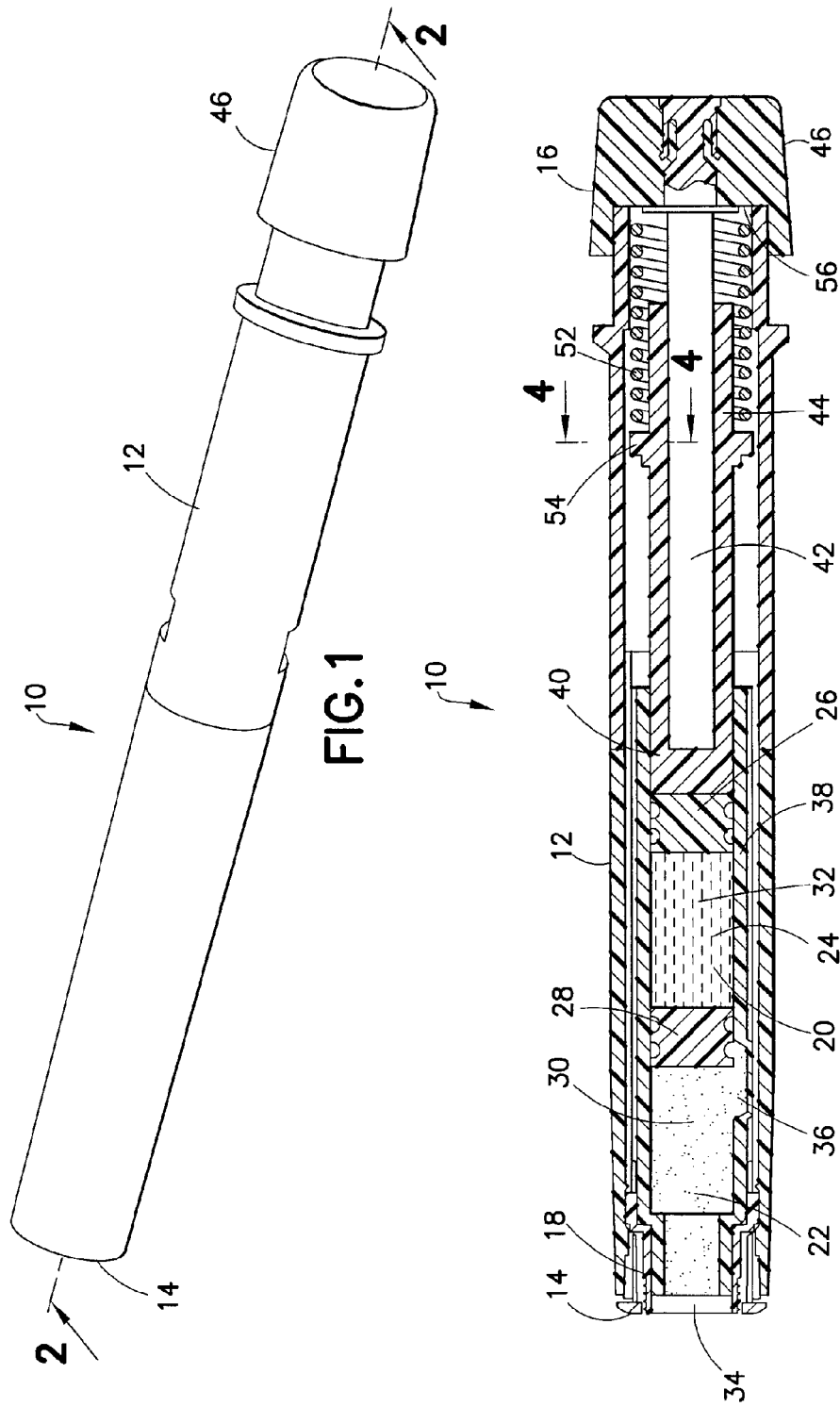

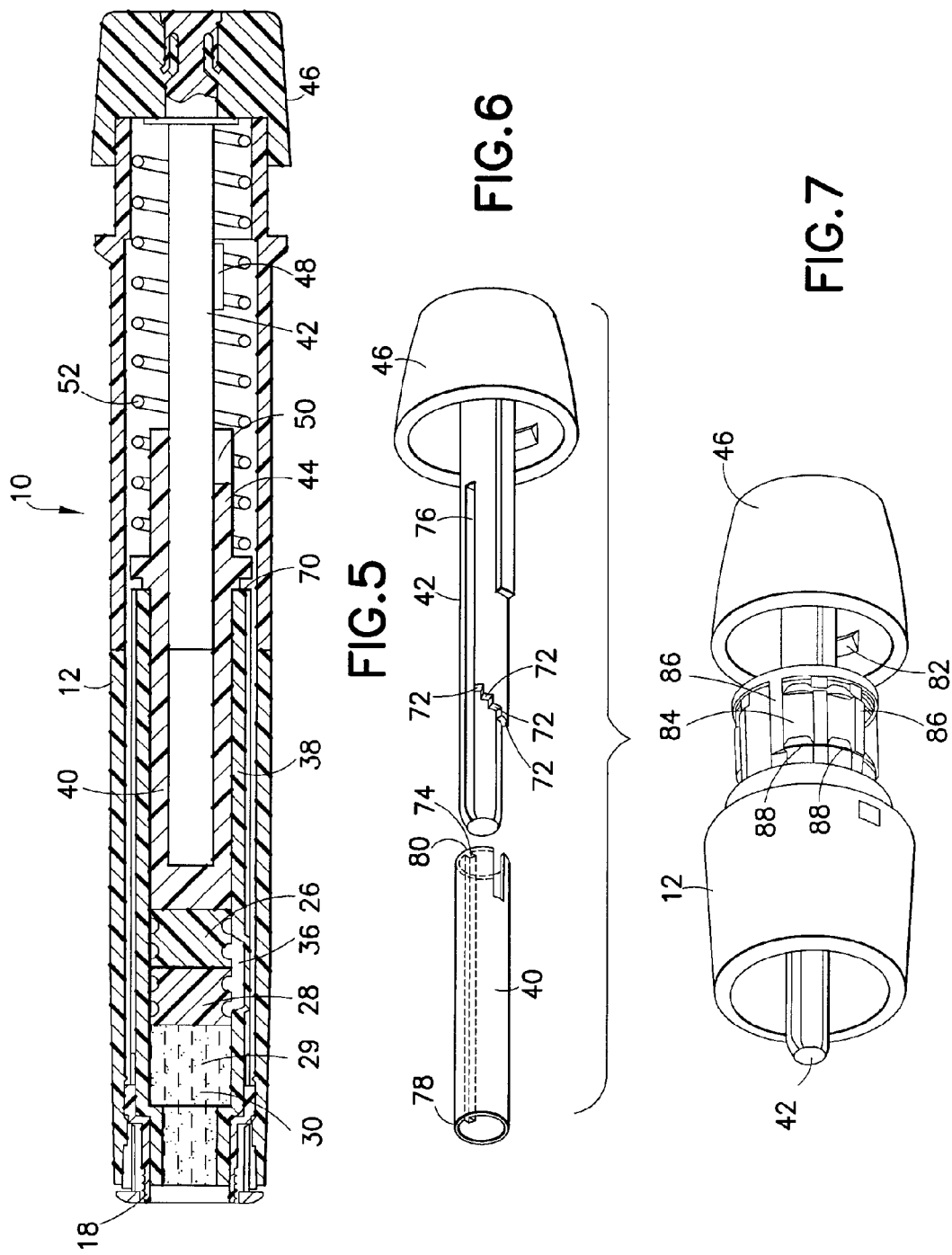

MEDICAL INJECTOR WITH DOSE KNOB ACTIVATION FOR AUTOMATED RECONSTITUTION

FIELD OF THE INVENTION

This invention relates to autoreconstitution devices and, more particularly, to autoreconstitution devices having dose-setting mechanisms.

BACKGROUND OF THE INVENTION

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder form that require reconstitution.

In addition, drugs may be provided as multipart systems which require mixing prior to administration. For example, one or more liquid (e.g., flowable (slurry or liquid)) components, and/or dry (e.g., powdered or granular) components may be provided in a drug container or delivery device which require mixing prior to administration. The components can be mixed and used to form various administratable drugs, such as insulin.

Prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. U.S. Pat. No. 4,874,381 to Vetter is directed to an injector having a barrel configured for mixing, while U.S. Pat. No. 4,968,299 to Ahlstrand et al. is directed to a drug cartridge having a barrel configured for mixing. Both Vetter et al. and Ahlstrand et al. disclose typical configurations for mixing where a bypass channel is formed in the barrel of the device. As such, the device must be specifically configured for mixing.

Manual force may be applied to a reconstitution device to cause the mixing of the multiple components. In addition, autoreconstitution devices have been developed in the prior art which provide a trigger-activated automated reconstitution. U.S. Pat. No. 6,793,646 to Giambattista et al. is an example of an autoreconstitution device. U.S. Pat. No. 6,793,646 is incorporated by reference in its entirety herein. The Giambattista et al. injector includes telescoping upper and lower body portions. Autoreconstitution is achieved by telescopingly collapsing the body parts together, thus releasing a spring that forces the reconstitution. It has been found that the Giambattista et al. type device requires a fairly substantial amount of force to activate and is difficult for some. In addition, components occasionally get stuck, thus rendering the injector inoperable.

SUMMARY OF THE INVENTION

A medical injector is provided herein having a body with a proximal end and a distal end. A reservoir is disposed in the body, the reservoir including at least first and second mixable components. At least one stopper is associated with the reservoir where distal advancement of the stopper over a predetermined distance causes mixing of the mixable components. A plunger is disposed in the body, along with a knob stem and a knob fixed to the knob stem so as to be rotatable therewith. A sleeve is telescopingly disposed over the knob stem, wherein the knob stem and the sleeve have cooperating elements formed thereon which selectively permit rotation of the knob stem to be transmitted to the sleeve so that the knob stem and the sleeve may rotate together. A spring is also provided for urging the sleeve distally. A releasable retainer releasably retains the sleeve in a first position against force of the spring. The releasable retainer includes a detent formed on one of the body and the sleeve, and, a channel formed in the other of the body and sleeve. The channel has a first part disposed partially circumferentially about a longitudinal axis of the sleeve, and a second part extending from the first part and disposed generally parallel to the longitudinal axis. The channel is formed to receive the detent and to permit sliding movement of the detent therealong. The sleeve is retained in the first position with the tab being located in the first part of the channel. Rotation of the knob causes the detent to move into the second part of the channel thus allowing the spring to displace the sleeve distally. Distal movement of the sleeve causes distal movement of the plunger which causes distal movement of the stopper thus causing mixing of the mixable components. Advantageously, with the subject invention, a medical injector may be provided where autoreconstitution can be achieved by the turning of a knob.

These and other features of the invention will be better understood through a study of the following detailed description and accompanying drawings.

BRIEF DESCRIPTION OF THE DRAWINGS

FIG. 1 is a perspective view of a medical injector formed in accordance with the subject invention;

FIG. 2 is a cross-sectional view taken along line 2-2 of FIG. 1;

FIG. 5 is a cross-sectional view showing the medical injector in a state after reconstitution;

FIG. 6 is a schematic view of a plunger and dose setting component useable with the subject invention; and, FIG. 7 is a schematic view of a portion of an injector body and a dose setting component useable with the subject invention.

DETAILED DESCRIPTION OF THE INVENTION

Figure 3:
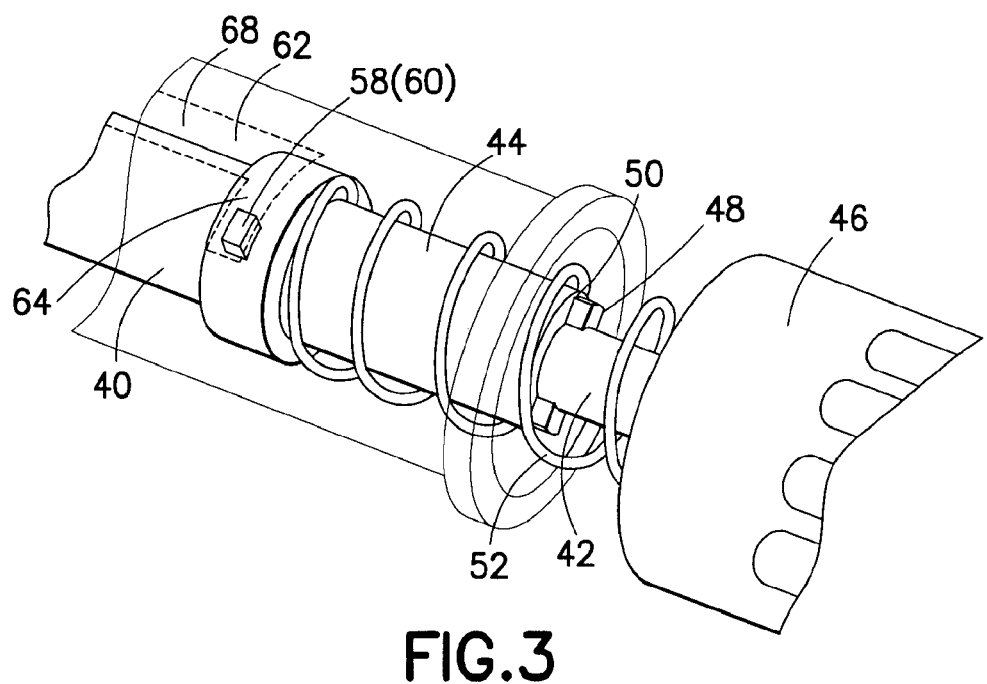
FIG. 3 is a schematic view of a releasable retainer useable with the subject invention.

With reference to the figures, a medical injector 10 is shown having a body 12 with a distal end 14 and a proximal end 16. The distal end 14 is intended to be directed towards a patient during use while the proximal end 16 is intended to be directed away from a patient during use. The medical injector 10 includes features 18 to which a needle assembly may be mounted in any known manner, such as threads.

A reservoir 20 is disposed in the body 12 for accommodating first and second mixable components 22, 24. At least one stopper 26 is associated with the reservoir 20 configured such that distal advancement of the stopper 26 over a predetermined distance shall cause mixing of the first and second mixable components 22, 24. Any known arrangement for allowing such mixing may be utilized. By way of non-limiting example, the first and second mixable components 22, 24 may be separated by a secondary stopper 28. The secondary stopper 28 divides the reservoir 20 into first and second chambers 30, 32, respectively, accommodating the first and second mixable components 22, 24. A septum 34 seals off the distal end of the first chamber 30, while the stopper 26 is positioned to seal off the proximal end of the second chamber 32. Preferably, if a dry component is used as one of the mixable components, the dry mixable component is located in the first chamber 30.

One or more by-pass channels 36 are formed in the wall of the reservoir 20. In an initial state, as shown in FIG. 2, the secondary stopper 28 is located at least partially proximally of the by-pass channels 36 so as to define a seal between the first and second chambers 30, 32 and to define a seal between the second chamber 32 and the by-pass channels 36. With distal advancement of the stopper 26, and with the second mixable component 24 being wet and generally incompressible, force of movement of the stopper 26 is transmitted to the secondary stopper 28 through the second mixable component 24. With sufficient distal movement of the secondary stopper 28, the second chamber 32 comes into communication with the by-pass channels 36, thus allowing the second mixable component 24 to be urged into the first chamber 30 with further distal movement of the stopper 26. With reference to FIG. 5, with sufficient distal advancement of the stopper 26, the second chamber 32 is collapsed with none or substantially none of the second mixable component 24 remaining therein. In addition, the secondary stopper 28 is located so as to define a seal between the first chamber 30 and the by-pass channels 36. The first and second mixable components 22, 24 are mixed within the first chamber 32, such as through agitation of the medical injector 10, so as to produce an injectable solution 29, ready for injection.

The reservoir 20 is defined in a barrel 38. The barrel 38 may be the barrel of a separate drug cartridge (FIG. 2) or a portion of the medical injector 10.

As will be recognized by those skilled in the art, other arrangements for permitting reconstitution may be utilized. In addition, more than two-part systems, such as three-part and so forth, systems may be utilized. Active medical ingredients may be included in one or both of the first and second mixable components 22, 24. The first mixable component 22 may be dry (e.g., a powder or granular substance) and/or a liquid (e.g., flowable (slurry or liquid)). As mentioned above, the second mixable component 24 is preferably only a wet flowable component such as a liquid or slurry.

A tubular plunger 40 is positioned and configured to engage the stopper 26. A knob stem 42 is provided which, preferably, extends into at least a portion of the plunger 40. A sleeve 44 is telescopingly disposed over the knob stem 42 and configured to engage the plunger 40. A knob 46 is fixed to the knob stem 42 so as to be rotatable therewith. The knob 46 is located exteriorly of the body 12 and proximate to the proximal end 16.

The knob stem 42 and the sleeve 44 have cooperating elements formed thereon which selectively permit rotation of the knob stem 42 to be transmitted to the sleeve 44 so that the knob stem 42 and the sleeve 44 may rotate together. In a preferred arrangement, a protrusion 48 extends from the knob stem 42 which is received in a slot 50 formed in the sleeve 44. The interengagement of the protrusion 48 and the slot 50 causes the sleeve 44 to rotate with the knob stem 42. As shown in FIG. 5, and discussed below, with distal displacement of the sleeve 44, the protrusion 48 is configured to be removed from the slot 50 so as to permit rotation of the knob stem 42 separate from the sleeve 44. As will be appreciated by those skilled in the art, the protrusion 48 may be formed on the sleeve 44 and the slot 50 may be formed on the knob stem 42 as an alternative.

A spring 52 is provided to distally urge the sleeve 44. It is preferred that the spring 52 be located about the sleeve 44 to act between sleeve shoulder 54 and rear face 56. The spring 52 may be a coil or compression spring. Alternatively, as recognized by those skilled in the art, various biasing elements may be utilized as the spring.

Figure 4:
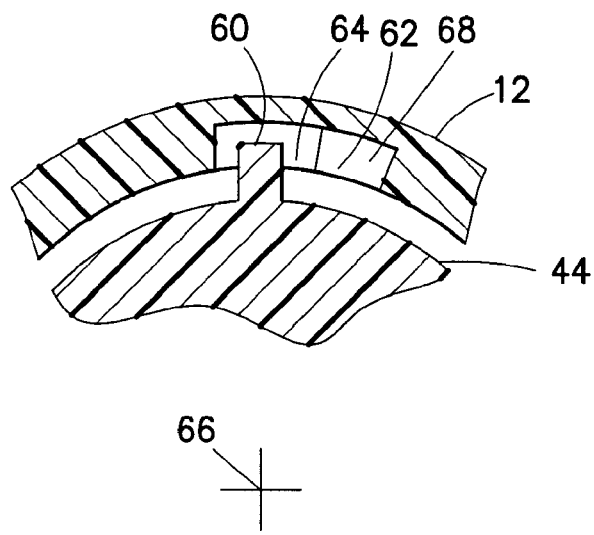
FIG. 4 is a partial cross-sectional view taken along line 4-4 of FIG. 2.

FIG. 2 shows the sleeve 44 being retained in a first position against force of movement generated by the spring 52. A releaseable retainer 58 is provided which retains the spring 52 in the first state. With reference to FIGS. 3 and 4, the releaseable retainer 58 includes a detent 60 located on the sleeve 44, preferably adjacent to the sleeve shoulder 54, and a channel 62 formed in the body 12. The channel 62 includes a first part 64 which partially extends about a longitudinal axis 66 of the sleeve 44. The channel 62 also includes a second part 68 which extends from the first part 64 and is generally parallel to the longitudinal axis 66. The channel 62 may have a general L-shape. The channel 62 is formed to receive the detent 60 and to permit sliding movement of the detent 60 therealong. The arrangement of the detent 60 and the channel 62 may be reversed with the detent 60 located on the body 12 and the channel 62 located on the sleeve 44.

With reference to FIGS. 3 and 4, the detent 60 is shown to be nested in the first part 64 of the channel 62. In this state, the sleeve 44 is retained in the first position. With rotation of the knob 46, the knob stem 42 is caused to rotate, and, in turn, the sleeve 44 is caused to rotate. Such rotation causes the detent 60 to move into the second part 68 of the channel 62 thus allowing the spring 52 to distally advance the sleeve 44. As shown in FIG. 5, the sleeve 44 is advanced distally causing the plunger 42 to advance distally, and, in turn, causing the stopper 26 to advance distally thus causing mixing of the first and second mixable components 22, 24. Distal movement of the sleeve 44 under force of the spring 52 may be limited due to interengagement of the sleeve shoulder 54 with a stop surface 70 formed on the body 12 and/or engagement with the barrel 38.

It is preferred that the mixing of the components be conducted without a needle mounted to the medical injector 10. As such, the reservoir 20 is not vented during the mixing. With a needle being mounted to the medical injector 10 after the mixing, any residual gases trapped in the reservoir 20 are purged through the needle. It may be preferred to not provide a physical stop to the distal advancement of the plunger 40. In this manner, the mixed components may be maximally compressed under force of the spring 52. With mounting of a needle onto the medical injector 10, the reservoir 20 is vented thus permitting further distal advancement of the plunger 40. This secondary distal advancement may assist in priming a needle for use.

Once mixed, the size of a dose to be administered by the medical injector 10 may be adjusted. With reference to FIG. 6, the knob stem 42 is provided with a plurality of axially and radially spaced-apart abutment surfaces 72. The abutment surfaces 72 correspond to different administrable dosage amounts. An engagement surface 74 is defined on the plunger 40. Rotation of the knob stem 42 causes radial displacement of the abutment surfaces 72. The abutment surfaces 72 are axially alignable with the engagement surface 74 such that with sufficient distal displacement of the knob stem 42 at least one of the abutment surfaces 72 will be caused to engage the engagement surface 74 and transmit force of movement to the plunger 40. In this manner, distal displacement of the knob stem 42 may be transmitted to the plunger 40. Moreover, stroke length corresponding to the movement of the plunger 40 may be adjusted depending on the abutment surface 72 which is in engagement with the engagement surface 74. The greater the initial distance of the abutment surfaces 72 from the engagement surface 74, the corresponding smaller dose that will be caused to be administered. Regardless of the selected dose amount, it is preferred that the knob stem 42 having a fixed length of stroke for distal displacement during administration of an injection. The further abutment surfaces 72 have greater lost motion with distal movement of the knob stem 42 and, thus, less distance engaging the engagement surface 74. The extent of movement of the plunger 40 dictates the extent of movement of the stopper 26 and, thus, dictates the amount of the injectable solution 29 to be driven from the reservoir 20 in an injected dose.

The dose is selected by rotating the dose knob 46. Indicia may be provided on the body 12 and/or the dose knob 46 in facilitating dose setting. To prevent the dose knob from being inadvertently turned prior to mixing of the mixable components 22, 24, the knob stem 42 may be coupled to the sleeve 44 so as to prevent relative rotation therebetween, as described above. With reconstitution, the sleeve 44 may decouple from the knob stem 42 so as to permit relative rotation therebetween. In addition, with reference to FIG. 6, a groove 76 may be formed in the knob stem 42 corresponding to a rib 78 formed on the plunger 40. In an initial state, as shown in FIG. 2, the rib 78 nests within the groove 76 so as to prevent relative rotation between the plunger 40 and the knob stem 42. With reconstitution being completed, the plunger 40 may be advanced so as to have the rib 78 removed from the groove 76. The knob stem 42 is then free to rotate in setting a dose. Alternatively, the rib 78 may still be partially nested in the groove 76 even in a post-reconstituted state. With this configuration, the knob stem 42 is proximally displaced to have the rib 78 removed from the groove 76 thus permitting subsequent dose setting. The dose is administered by causing distal advancement of the knob 46 once the dose has been properly set.

It is noted that the engagement surface 74 may be located at a proximal end 80 of the rib 76.

It is preferred that the knob 46 be releasably retained in positions corresponding to the various dose settings. In this manner, it is preferred that once a dose has been set, there is no rotation of the knob 46 during distal displacement thereof, thus avoiding that an improper of the abutment surfaces 72 engage the engagement surface 74. Such an arrangement is disclosed in U.S. Pat. No. 6,793,646. As shown in U.S. Pat. No. 6,793,646, with reference to FIG. 7, one or more tabs 82 may be formed on the knob 46 which are selectively engageable with positioning channels 84 formed on a portion of the body 12. Positioning channels 84 are circumferentially separated by dividers 86 and positioned to correspond to the abutment surfaces 72. The tabs 82 nest in the positioning channels 84 at given radial positions of the knob 46 corresponding to different dose sizes. With turning of the knob 46, the tabs 82 are caused to by-pass the dividers 86 and move into a corresponding of the positioning channels 84. The positioning channels 84 maintain the radial position of the knob 46.

In addition, it is preferred that the knob 46 be maintained in an axial position so as to permit a fixed stroke length of distal advancement for dose administration. One or more retaining ribs 88 may be located along the positioning channels 84 so as to limit axial movement of the tabs 82. With a dose having been selected, the knob 46 may be distally advanced with the tabs 82 by-passing the retaining ribs 88. It is preferred that the tabs 82 and the retaining ribs 88 be configured so as to provide a locking affect so as to prevent rearward retraction of the knob 46 and re-use of the medical injector 10.

As will be understood by those skilled in the art, the body 12 may be formed of one or more components with the features described herein being formed on any of those one or more components.

What is claimed is:

1. A medical injector comprising:
   a body having a proximal end and a distal end;
   a reservoir disposed in said body, said reservoir including at least first and second mixable components, at least one stopper being associated with said reservoir, distal advancement of said stopper a predetermined distance causing mixing of said mixable components;
   a plunger disposed in said body;
   a knob stem disposed in said body;
   a knob fixed to said knob stem so as to be rotatable therewith;
   a sleeve telescopingly disposed over said knob stem and configured to engage said plunger, wherein said knob stem and said sleeve having cooperating elements formed thereon which selectively permit rotation of said knob stem to be transmitted to said sleeve so that said knob stem and said sleeve may rotate together;
   a spring for urging said sleeve distally; and,
   a releaseable retainer for releasably retaining said sleeve in a first position against force of said spring, said releaseable retainer including:
     a detent formed on one of said body and said sleeve; and,
     a channel formed in the other of said body and said sleeve, said channel having a first part disposed partially circumferentially about a longitudinal axis of said sleeve, and a second part extending from said first part and disposed generally parallel to said longitudinal axis, said channel being formed to receive said detent and to permit sliding movement of said detent therealong;
   wherein, said sleeve is retained in said first position with said detent being located in said first part of said channel, and,
   wherein, rotation of said knob causes said detent to move into said second part of said channel thus allowing said spring to displace said sleeve distally, distal movement of said sleeve causing distal movement of said plunger which causes distal movement of said stopper thus causing mixing of said mixable components.

2. A medical injector as in claim 1, wherein said knob is located exteriorly of said body and proximate to said proximal end.

3. A medical injector as in claim 1, wherein distal movement of said sleeve causes said cooperating elements to separate, thus, permitting said plunger to rotate separately from said sleeve.

4. A medical injector as in claim 1, wherein said knob stem includes a plurality of axially and radially spaced-apart abutment surfaces, said plunger including an engagement surface, said abutment surfaces being axially alignable with said engagement surface such that sufficient distal displacement of said knob stem causes at least one of said abutment surfaces to engage said engagement surface and to cause distal displacement of said plunger, which in turn, causes distal displacement of said stopper.

* * * * *

UNITED STATES PATENT AND TRADEMARK OFFICE
CERTIFICATE OF CORRECTION

PATENT NO. : 8,403,883 B2  Page 1 of 1
APPLICATION NO. : 13/119014
DATED : March 26, 2013
INVENTOR(S) : Fayyaz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 156 days.

Signed and Sealed this
First Day of September, 2015

Michelle K. Lee
*Director of the United States Patent and Trademark Office*